(12) United States Patent
Fieres

(10) Patent No.: US 8,530,864 B2
(45) Date of Patent: Sep. 10, 2013

(54) OPTIMIZATION OF CONTROL PARAMETERS FOR A PARTICLE IRRADIATION SYSTEM

(75) Inventor: Johannes Fieres, Heidelberg (DE)

(73) Assignee: Siemens Aktiengesellschaft, München (DE)

( * ) Notice: Subject to any disclaimer, the term of this patent is extended or adjusted under 35 U.S.C. 154(b) by 255 days.

(21) Appl. No.: 12/708,296

(22) Filed: Feb. 18, 2010

(65) Prior Publication Data

US 2010/0213394 A1  Aug. 26, 2010

(30) Foreign Application Priority Data

Feb. 24, 2009  (DE) .......................... 10 2009 010 284

(51) Int. Cl.
*A61N 5/10* (2006.01)
(52) U.S. Cl.
USPC .................................. 250/492.1; 250/492.22
(58) Field of Classification Search
USPC ........... 250/492.1, 492.22, 492.3; 378/64–65
See application file for complete search history.

(56) References Cited

U.S. PATENT DOCUMENTS

| | | | |
|---|---|---|---|
| 5,647,663 A | 7/1997 | Holmes | |
| 5,818,902 A | 10/1998 | Yu | |
| 6,741,674 B2 * | 5/2004 | Lee | 378/65 |
| 8,039,822 B2 * | 10/2011 | Rietzel | 250/492.3 |
| 8,217,373 B2 * | 7/2012 | Bert et al. | 250/492.3 |
| 8,299,448 B2 * | 10/2012 | Bert et al. | 250/492.3 |
| 8,405,050 B2 * | 3/2013 | Bert et al. | 250/491.1 |
| 2005/0207531 A1 | 9/2005 | Dempsey et al. | |
| 2007/0201614 A1 * | 8/2007 | Goldman et al. | 378/65 |
| 2008/0298550 A1 * | 12/2008 | Otto | 378/65 |
| 2010/0213394 A1 * | 8/2010 | Fieres | 250/492.3 |
| 2011/0297849 A1 * | 12/2011 | Bert et al. | 250/492.1 |
| 2012/0241635 A1 * | 9/2012 | Luechtenborg et al. | 250/389 |

FOREIGN PATENT DOCUMENTS

| | | | |
|---|---|---|---|
| EP | 1818078 A1 * | 8/2007 | |
| WO | WO 2008/039991 A9 | 4/2008 | |
| WO | WO 2008116535 A1 * | 10/2008 | |

OTHER PUBLICATIONS

European Patent Office Search Report and Written Opinion dated Jun. 24, 2010 for EP 09178624.4 with English translation.
Chvetsov, A. V. et al., "Optimization of equivalent uniform dose using the L-curve criterion," Phys. Med. Biol., vol. 52, No. 19, 2007, pp. 5973-5984.
Krämer, M., et al., "Treatment planning for heavy-ion radiotherapy: physical beam model and dose optimization." Phys. Med. Biol. 45, pp. 3299-3317. (2000).
German Office Action dated Feb. 11, 2010 with English translation.
Zhu, Lei, et al., "Using total-variation regularization for intensity modulated radiation therapy inverse planning with field-specific numbers of segments," Phys. Med. Biol. 53, pp. 6653-6672, Stanford, CA 2008.

* cited by examiner

*Primary Examiner* — David A Vanore
*Assistant Examiner* — Wyatt Stoffa
(74) *Attorney, Agent, or Firm* — Lempia Summerfield Katz LLC

(57) ABSTRACT

A device for determining control parameters for a particle irradiation system that deposits different dose values at different target points in a target volume through the selection of sampling points by a particle beam is provided. The device includes an input for receiving information relating to a predefined dose distribution via target points, and a determination component for determining a particle number distribution that is to be deposited during the irradiation via sampling points. The determining takes place using the predefined dose distribution and a variable, which takes into account differences in the particle number distribution between particle numbers of different sampling points.

20 Claims, 4 Drawing Sheets

OPTIMIZATION OF CONTROL PARAMETERS FOR A PARTICLE IRRADIATION SYSTEM

The present patent document claims the benefit of DE 10 2009 010 284.1, filed Feb. 24, 2009, which is hereby incorporated by reference.

BACKGROUND

The present embodiments relate to a device and a method for determining control parameters for a particle irradiation system.

Particle therapy is an established method for treating tissue, in particular tumorous diseases. Irradiation methods, as used in particle therapy, are also used in non-therapeutic areas. The non-therapeutic areas include, for example, research activities (e.g., for product development) in the field of particle therapy, which are performed on non-living phantoms or bodies, and irradiation operations on materials. In the applications, charged particles (e.g., protons, carbon or other ions) are accelerated to high energies, shaped into a particle beam and conducted via a high-energy beam transport system to one or more irradiation rooms. In an irradiation room, an object to be irradiated is irradiated in a target volume with the particle beam.

SUMMARY AND DESCRIPTION

The present embodiments may obviate one or more of the drawbacks or limitations inherent in the related art. For example, in one embodiment, a device and a method for determining control parameters for a particle irradiation system may be disclosed. In another example, a method for irradiating a target volume with particles, as well as a computer program and a computer program product may be presented.

In one embodiment, a device serves for determining control parameters for a particle irradiation system. Different dose values may be deposited using the particle irradiation system at different target points in a target volume through selection of sampling points by a particle beam. The device may include an input for receiving a dose distribution via target points and a determination component for determining a particle number distribution to be deposited during an irradiation session via sampling points. The particle number distribution may be determined in such a way that both the predefined dose distribution and a variable are used. The variable may take differences between particle numbers of different sampling points into account, the differences corresponding to the determined particle number distribution.

The particle irradiation system may perform an irradiation with particles in a manner known. The particle irradiation system may be controlled in such a way that a dose is deposited at various target points of the volume that is to be irradiated, and a specific number of particles of a specific energy are sent in a specific direction. The combination of a specific particle energy with a specific send direction corresponds to a sampling point. The number of particles per sampling point is derived from the determined particle number distribution; the particle number distribution therefore assigns to at least some sampling points how many particles of a specific energy are to be sent in the direction corresponding to the sampling point. The determining of the control parameters may take place prior to the irradiation for the efficient execution of the irradiation treatment in accordance with the planning.

In order to determine a searched-for particle number distribution, the device uses at least two of:

A predefined dose distribution, which assigns at least to some target points, a dose that the target points are to receive during the irradiation session. The dose is, for example, a dose of energy that is expressed as energy absorbed per mass. Other dosage types may be used, such as, for example, an energy dose weighted with a biological efficacy.

A variable, which takes into account differences between particle numbers of different sampling points. The particle numbers are defined according to the determined particle number distribution. Using the variable, different sampling points are therefore compared in relation to one another in terms of the corresponding determined particle numbers.

The variable may take into account the differences between the particle numbers of sampling points in different ways. A common feature of the different ways is that at least one difference between a first particle number and a second particle number is input into the variable. The particle numbers may also be mean values.

In one embodiment, determination of control parameters may enable the duration of the treatment in the course of the irradiation session to be reduced. Also, the treatment plan may be made more robust against positioning inaccuracies. In real-world practice, inaccuracies in patient positioning may occur. Displacements of even 5 mm may lead to clinically unacceptable dose distributions. Plans produced using the determination of control parameters are more robust. In other words, the planned dose distribution may still be realized in spite of a poor positioning of the patient.

In one embodiment, the variable takes into account differences between particle numbers of different sampling points, which are to be irradiated with particles of the same energy in accordance with the particle number distribution. Different sampling points are compared in relation to the particle number using the variable, with the different sampling points being irradiated with particles of the same energy (e.g., corresponding to the concept of iso-energy planes). The comparison of the particle numbers therefore takes place within an iso-energy plane.

In one embodiment, the variable takes into account differences between particle numbers of all sampling points that are to be irradiated with particles of the same energy in accordance with the particle number distribution. The comparison of the particle numbers therefore takes place within an iso-energy plane, with sampling points of the plane being incorporated into the variable.

According to one embodiment, the variable contains a variation of particle numbers of different sampling points that are to be irradiated with particles of the same energy in accordance with the particle number distribution. The comparison of the particle numbers therefore takes place within an iso-energy plane, with consideration being given to how strong the scatter in the values for the particle numbers is within the iso-energy plane. For example, the variance may be used as a measure for the scatter. The variance, known from statistics, is computed by squaring the distances of the values from the mean value, then adding and dividing by the number of values.

In one embodiment, the variable may contain a value range of particle numbers of the sampling points that are to be irradiated with particles of the same energy in accordance with the particle number distribution. The comparison of the particle numbers therefore takes place within an iso-energy plane, with an examination of which value range is covered by the particle numbers. For example, the comparison of particle numbers may look at the maximum difference between the particle numbers of different sampling points (e.g., the difference between the sampling point with the highest particle number and the sampling point with the lowest particle number).

In one embodiment, the variable may contain a ratio between the highest particle number and the lowest particle number of sampling points that are to be irradiated with particles of the same energy in accordance with the particle number distribution. The comparison of the particle numbers therefore takes place within an iso-energy plane, with an examination of how the highest particle number within the iso-energy plane relates to the smallest particle number within the iso-energy plane.

In other embodiments, the variable may relate to one specific iso-energy plane, to a plurality of iso-energy planes, or to all iso-energy planes. In one embodiment, the variable may take the particle numbers into account in the above-described ways without the sampling points lying on the same iso-energy plane.

In one embodiment, the determination of control parameters is performed by optimizing a cost function that includes a first term relating to the predefined dose distribution, and a second term relating to the variable. Numerous methods for optimizing cost functions are known and may be used within the framework of the present embodiments. In one embodiment, the cost function may include a predefinable parameter for the purpose of a relative weighting of the first term in relation to the second term. The predefinable parameter, like the predefinable dose distribution, may be made available, for example, via the input of the device. In one embodiment, the cost function optimization optimizes the particle number distribution in terms of the predefined dose distribution and in terms of an irradiation duration. A relationship between the irradiation duration and the variable is produced, for example, when the irradiation is based on an at least temporarily constant particle intensity (e.g., a number of particles emitted per time unit).

In one embodiment, a method for determining control parameters is provided. Information relating to a predefined dose distribution is received via target points, where a particle number distribution that is to be deposited during the irradiation is determined via sampling points. The determination takes place using the predefined dose distribution and a variable which takes into account differences between particle numbers of the particle number distribution of different sampling points.

In one embodiment, a method for determining control parameters may be developed as explained above in relation to one embodiment of the device.

In one embodiment, a method for irradiating a target volume with particles is provided. The control parameters for controlling the particle irradiation system are determined as described above. The target volume may be either fully or partially a non-living body (e.g., a phantom, which is employed for verifying an irradiation plan).

In one embodiment, a computer program that has program code for performing one embodiment of the above-described methods when the computer program is executed on a computer may be provided.

In one embodiment, a computer program product includes program code that is stored on a tangible computer-readable data medium for performing one embodiment of the above-described methods when the computer program is executed on a computer.

DETAILED DESCRIPTION

Figure 1:
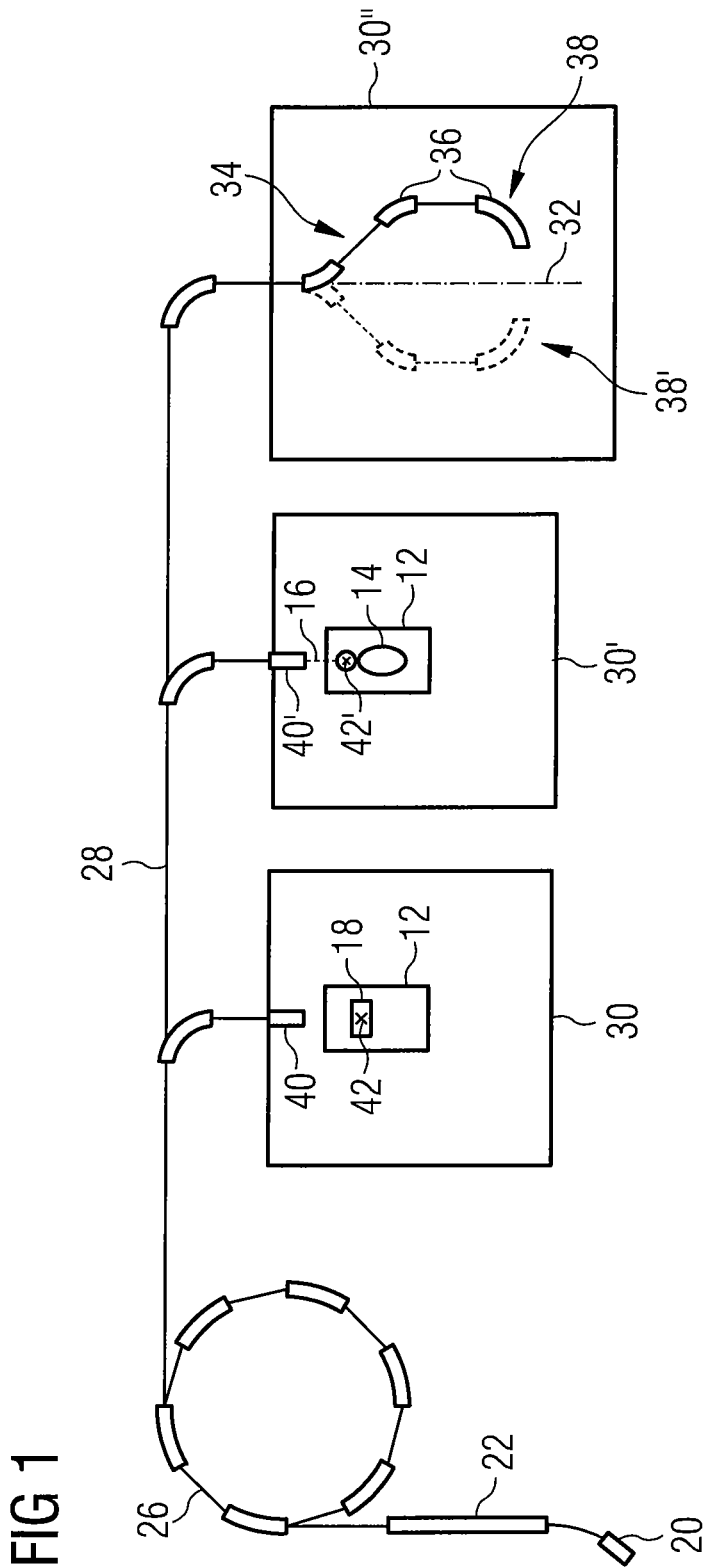
FIG. 1 shows a schematic view of one embodiment of a particle therapy system.

FIG. 1 shows a schematic representation of one embodiment of a particle therapy system. The particle therapy system is used for irradiating a patient 14 disposed on a positioning device 12 with a beam including particles 16 (e.g., a particle beam 16 or an ion beam). Tumor-diseased tissue of the patient 14 may be irradiated with the particle beam 16 using the particle therapy system. The particle irradiation system may also be used for irradiating a non-living object 18 (e.g., a water phantom 18). The water phantom 18 is irradiated, for example, for purposes of checking and verifying irradiation parameters before and/or after an irradiation treatment of the patient 14. The particle therapy system may also be provided to irradiate other objects (e.g., experimental setups such as cell cultures or bacteria cultures) with the particle beam 16 for research purposes.

The particles used may be, for example, protons, pions, helium ions, carbon ions or ions of other elements. The particles may be generated in a particle source or ion source 20. The ion beam or particle beam generated by the ion source 20 is accelerated to a first energy level in the preaccelerator 22. The preaccelerator 22 is a linear accelerator, for example. The particles are injected into an accelerator 26, for example, a circular accelerator (e.g., a synchrotron or cyclotron). In the accelerator 26, the particle beam is accelerated to an energy required for the irradiation. After the particle beam has exited the accelerator 26, a high-energy beam transport system 28 transports the particle beam into one or more irradiation rooms 30, 30', 30" with, for example, the positioning device 12 (e.g., a patient examination couch) being arranged in the one or more irradiation rooms 30, 30', 30" with the patient 14 or the phantom 18 (e.g., a body) for irradiation planning verification. In the irradiation room 30 or 30' (e.g., a fixed beam room), the body 14 or 18 is irradiated from a fixed direction, the body 14 or 18 being arranged in a stationary manner. A gantry 34 movably disposed (e.g., rotatably disposed) about an axis 32 is provided in the treatment room 30". The gantry 34 enables the body 14 or 18 that is to be irradiated, to be irradiated from different directions. The particle beam 16 may be rotated using a gantry beam guide 36 disposed in the gantry 34, around the body 14 or 18 that is to be irradiated. A first position 38 and a second position 38' are shown in FIG. 1 in order to represent the different positions of the gantry beam guide 36 of the gantry 34. Intermediate positions for the gantry beam guide 36, which for reasons of clarity are not shown, may also be possible on at least a semicircle above the body 14 or 18 that is to be irradiated, in an imaginary sphere or spheroid around the body 14 or 18 that is to be irradiated. The target volume that is to be irradiated may thus be irradiated from a plurality of directions normal to the axis 32. This is advantageous for geometric reasons.

In the irradiation room 30, 30', the particle beam emerges from one end (e.g., a beam exit 40, 40') of a vacuum system of the high-energy beam transport system 28 and strikes the target volume that is to be irradiated in the body 14 or 18. The target volume may be disposed in an isocenter 42, 42' of the respective irradiation room 30, 30'.

FIG. 1 illustrates the basic layout of one embodiment of a particle therapy system. Different embodiments are also possible. The embodiments described in the following may be used both in connection with the particle therapy system illustrated with reference to FIG. 1 and with other particle therapy systems.

Figure 2:
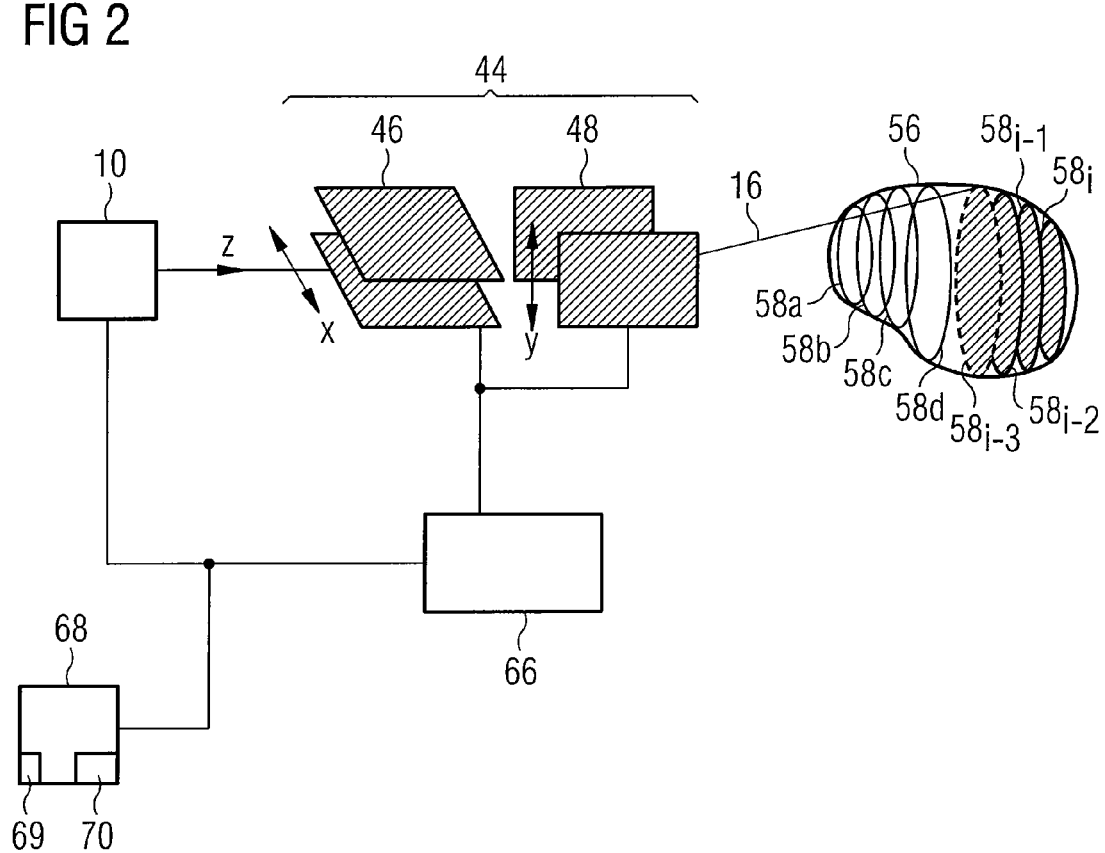
FIG. 2 shows a schematic view of an irradiation of a target volume using one embodiment of a raster scanning device.

FIG. 2 schematically shows an irradiation of a target volume 56. A raster scanning device 44 has a first particle beam deflection device 46 and a second particle beam deflection device 48, both of which devices may include magnets (e.g., scan magnets 46 and 48). The first and second particle beam deflection devices 46, 48 enable the particle beam 16 to be deflected horizontally and vertically, respectively. In FIG. 2, the arrows indicate the deflection direction of the particle beam 16 in the x-direction (e.g., horizontally) and in the y-direction (e.g., vertically). The raster scanning device 44 may thus scan or traverse a two-dimensional array including points having positions points $(x_j, y_j)$. The position points $(x_j, y_j)$ in combination with the particle energy used in each case may be defined as scan spots, raster points or sampling points. In other words, a sampling point is determined by the orientation of the particle beam 16 in the x-direction and y-direction, as well as by the particle energy. Accordingly, a plurality of sampling points exist for a combination of x and y values when particles of different energies are emitted.

The target volume 56 to be irradiated in the patient or object to be irradiated may be considered as including isoenergetic slices or layers 58a, 58b, 58c, . . . 58i. The iso-energy layers 58a, 58b, 58c, . . . 58i may, in each case, be assigned to a specific position on the z-axis. The layers are described as isoenergetic because particles of a specific starting energy interact mainly with a material of the respective layer (e.g., the energy dose of the particles having the specific starting energy acts to a great extent only on the respective iso-energy layer).

As shown in FIG. 2, the counting of the layers begins at the side facing the raster scanning device 44 with 58a, while the layer furthest from the raster scanning device 44 (e.g., a distal layer) has the designation 58i, where i denotes a number of layers. In order to adjust the particle beam 16 to a respective layer 58a, 58b, 58c, . . . 58i, the particle beam 16 has, in each case, a different starting energy, with the starting energy being that of the particles prior to the interaction with the object 14 or 18. The particle beam 16 with the lowest energy is deposited in the iso-energy layer 58a, and the particle beam 16 with the highest energy is deposited in the iso-energy layer 58i.

The irradiation using a scan method makes use of a particle beam 16, which is dimensioned such that a single dose can be deposited in the target volume 56 at a small, circumscribed region. The small region corresponds to a target point, with the coordinates of the target points being known for the irradiation planning. Accordingly, a specific target point may be irradiated by selecting a specific sampling point.

In order to irradiate the target volume 56, the different sampling points are selected successively. The particle beam 16 is deflected with the aid of the scan magnets 46 and 48 and thus guided over the target volume 56. In order to irradiate different iso-energy layers, the energy of the particle beam 16 is adjusted as appropriate. FIG. 2 shows a target volume 56 in which three distal iso-energy layers $58_i$, $58_{i-1}$, $58_{i-2}$ have already been irradiated, and in which the particle beam 16 is currently scanning across the subsequent iso-energy layer $58_{i-3}$.

Prior to the irradiation of a target volume 56, irradiation planning is carried out in order to control the irradiation (e.g., the scanning or sampling of the target volume 56 using the particle beam 16 in accordance with the irradiation plan produced). Irradiation planning therefore represents the determining of control parameters for the purpose of controlling the irradiation system 10. The irradiation planning is carried out using an irradiation planning device 68. The irradiation planning device 68 is, for example, a desktop computer, a workstation or another computer. The irradiation planning device 68 determines the control parameters that are used for controlling the subsequent irradiation.

The control parameters are forwarded to the irradiation device 10 for the purpose of performing the irradiation. The irradiation planning device 68 may not be physically connected to the irradiation device 10, as shown in FIG. 2. Rather, the computation results produced by the irradiation planning device 68 may be transferred to the irradiation device 10 through a data medium. There may also be a time gap (e.g., several days) between planning and irradiation.

The irradiation device 10 is controlled by a control and monitoring system, which includes individual subordinate control devices for different subsystems. The individual subordinate control devices include, for example, the control device 66 for the raster scanning device 44 and may include other additional control devices (not shown for clarity of illustration reasons) for other parts of the irradiation device 10. The control and monitoring system controls the course of the irradiation treatment in accordance with the control parameters determined by the irradiation planning device 68.

In one embodiment, the location and extent of a tumor or another target volume 56 that is to be irradiated are determined using a computed tomography or magnetic resonance imaging scanner or other diagnostic equipment (e.g., imaging devices). The irradiation planning device 68 receives data from the imaging devices via an input 69.

In one embodiment, the irradiation planning device 68 may also include a user interface 70 to enable a user to specify the target volume(s) 56 and a dose distribution that is to be applied. The user can therefore specify an energy dose for the target points of the target volume 56 (e.g., a target dose distribution).

The irradiation planning device 68 determines the control parameters for the irradiation on the basis of the target dose distribution. The irradiation planning device 68 determines how many particles of a specific energy are to be emitted for each sampling point. The irradiation planning device 68 may take into account that the intensity of the particle beam (e.g., the number of particles per second) within each iso-energy layer remains constant. The intensity may therefore be adjusted to the sampling point having the smallest number of particles within the iso-energy layer. If sampling points having a significantly higher number of particles exist within the iso-energy layer, the sampling points having a significantly higher number of particles may be irradiated for a long period of time, as a result of the constant intensity.

An irradiation session that lasts for a long period of time may be unpleasant for a patient. The patient may be held in a fixed position during the irradiation so that movements of the target volume may be excluded. In order to avoid long irradiation times, care should therefore be taken to ensure that the dynamics of the particle numbers within each iso-energy layer are small. The dynamics of the particle numbers may be expressed in different ways, for example, as the ratio of greatest to smallest particle number of the sampling points within the iso-energy layer, the distance between the greatest and smallest particle number of the sampling points within the iso-energy layer, or the variance of the particle numbers within an iso-energy layer.

During irradiation planning, therefore, two opposing interests are present when the particle numbers are being determined: a best possible dose distribution, which may be defined by a dose distribution as close as possible to the predefined target dose distribution, and low particle dynamics within each iso-energy layer, corresponding to a short irradiation duration for the iso-energy layer (e.g., two optimization objectives).

The irradiation planning device 68 uses an optimization method for determining the particle numbers to be applied during the irradiation. In order to take the dose distribution and the particle dynamics into account, the following cost function F(I) is used:

$$F(I) = \sum_i \lfloor s_i(\Delta d_i(I))^2 \rfloor + \alpha \cdot R(I)$$

In the cost function F(I), I=[$I_1, I_2, \ldots, I_N$] is the N-tuple of the determined particle numbers (e.g., the particle number distribution). The variable I is determined and output as result. For example, $I_1$ is the number of particles that are to be used for the first sampling point, $I_2$ is the number of particles that are to be used for the second sampling point, etc. N sampling points are present for the iso-energy layers together.

The cost function F(I) is a function of free optimization parameters (e.g., a function of the particle numbers $I_i$ at all sampling points i). The cost function is a measure for the negative quality (e.g., a "poorness") of I. In order to determine a suitable particle number distribution I, the cost function F(I) is minimized with known methods (e.g., as described in Krämer, M, et al., "Treatment planning for heavy-ion radiotherapy: physical beam model and dose optimization." Phys. Med. Biol. 45, 3299-3317 (2000)).

The following applies with regard to the first summand of the cost function F(I). The index i relates to the target points. If, for example, target dose values were input for M points, i runs from 1 to M. $\Delta d_i(I)$ is the deviation between the dose of the target point i for the determined particle numbers I=[$I_1, I_2, \ldots I_N$] and the respective target dose of the target point i. In other words, the squared deviations of the actual from the desired dose values are considered. The term $s_i$ refers to weighting factors, which may take into account that some target points are more important than others in terms of maintaining the predefined target dose. If, for example, a sensitive organ (e.g., an organ, which should be exposed to as small a dose as possible) is disposed within the irradiation volume, then target points within the sensitive organ may be assigned a higher weighting factor. An example of the sensitive organ would be a brain stem, for which, for example, a target dose of close to zero may be specified by the user.

The first summand of the cost function, therefore, takes into account how far removed a determined dose distribution is from the target dose distribution. Thus, allowance is made for the best possible dose distribution.

The following applies with regard to the second summand of the cost function F(I). R is a regularization term, which takes into account the low particle number dynamics. The regularization term R may be calculated in several ways. In one embodiment, R is composed as follows:

$$R = \sum_E \beta(E)\sigma^2\left(\frac{I_E}{\langle I_E \rangle}\right)$$

An index E represents the iso-energy layer. In order to calculate R, therefore, summing is performed across the iso-energy layers. Accordingly, $I_E$ is a subtuple of I and contains only those values of the particle number distribution I that belong to the sampling points of the respective iso-energy layer E. The function $\sigma^2(x)$ calculates the variance of a tuple x, and $\langle x \rangle$ calculates a mean value of the elements of a tuple x of size M, for example, $$\langle x \rangle = \frac{1}{M}\sum_{i=1}^{M} x_i.$$

In order to achieve independence from the absolute particle numbers, a normalization is performed with respect to the mean value. A normalized quantity, $$\frac{I_E}{\langle I_E \rangle},$$

is computed rather than the variance of $I_E$.

A weighting factor β(E) is determined via $$\beta(E) = \frac{\text{Number of raster points in iso} - \text{energy layer } E}{\text{Total number of raster points } N}.$$

As a result of the weighting factor β(E), iso-energy layers having few sampling points are assigned a lower significance than iso-energy layers having many sampling points. Unfavorable (e.g., high) dynamics may have a greater effect on the length of time of the irradiation within a large iso-energy layer than in a small iso-energy layer (e.g., an iso-energy layer having few sampling points).

The regularization term R, therefore, includes a weighted sum over the iso-energy layers of the normalized variances of the determined particle numbers. The normalized variances may be used for estimating the particle dynamics since the normalized variances are a measure for the scatter of the determined particle numbers within an iso-energy layer. The second summand is thus a term in the cost function F(I), which penalizes high particle number dynamics. As a result, during the minimization of the cost function, solutions in the form of particle number distributions I, which are characterized by low dynamics, are favored.

The term α is a parameter greater than or equal to zero, which weights the first summand and the second summand of the cost function F(I) relative to one another. The parameter α may be specified by the user. In one embodiment, the user may specify a specific target dose distribution and a specific value for α, whereupon a particle number distribution I is determined by minimizing the cost function F(I). For the determined particle number distribution I, it may subsequently be indicated to the user how close the user comes to the target dose distribution when I is used and how much time the irradiation may take (e.g., a result). If the user agrees with the result, the irradiation may be performed in accordance with the determined particle number distribution I. In order to achieve a better approximation to the target dose distribution, the user may reduce the value for α; in order to reduce the time required for the irradiation, the user may increase the value for α. With a new value for the parameter α, the particle number distribution I is determined once again by minimizing a new cost function F(I). A continuously variable weighting of the two optimization objectives (e.g., optimal dose distribution and low particle number dynamics) relative to one another is therefore possible.

Mathematical aspects of the optimization are considered below. For many efficient optimization methods (e.g., gradient-based methods), the derivation of K to I is calculated.

First, the calculation of the derivation of $\sigma^2(I_E/\langle I_k \rangle)$ to I is explained. A single iso-energy layer is considered initially, so the index E may be omitted.

Using $\sigma^2(x) = \langle x^2 \rangle - \langle x \rangle^2$, the variance of the normalized particle number $$\frac{I}{\langle I \rangle}$$

is determined as:

$$\sigma^2 = \left(\frac{I}{\langle I \rangle}\right) = \left\langle \left(\frac{I}{\langle I \rangle}\right)^2 \right\rangle - \left\langle \frac{I}{\langle I \rangle}\right\rangle^2 = \frac{\langle I^2 \rangle}{\langle I \rangle^2} - 1$$

The squaring of a tuple may be defined as that tuple which contains the squares of the elements: $I^2 = [I_1^2, \ldots, I_N^2]$.

If the variance is derived with respect to $I_k$ (e.g., if the change in the variance is considered when there is a change in the particle number of the sampling point k), the following is obtained:

$$\frac{\partial \sigma^2}{\partial I_k} = \frac{1}{\langle I \rangle^2} \cdot \frac{\partial \langle I^2 \rangle}{\partial I_k} + \langle I^2 \rangle \cdot \frac{\partial}{\partial I_k}\left(\frac{1}{\langle I \rangle^2}\right)$$

$$= \frac{1}{\langle I \rangle^2} \cdot \frac{2 I_k}{N} + \langle I^2 \rangle \cdot \frac{-2}{\langle I \rangle^3 N}$$

$$= \frac{2}{N \langle I \rangle^2}\left(I_k - \frac{\langle I^2 \rangle}{\langle I \rangle}\right).$$

An optimization parameter w may be used instead of I, where $w^2 = I$. Accordingly, the determined result for I does not contain negative particle numbers. The derivation thus becomes:

$$\frac{\partial \sigma^2}{\partial w_k} = 2 w_k \cdot \frac{\partial \sigma^2}{\partial I_k} = \frac{4 w_k}{N \langle I \rangle^2}\left(I_k - \frac{\langle I^2 \rangle}{\langle I \rangle}\right).$$

Thus, the derivation of the regularization term R yields:

$$\frac{\partial R}{\partial w_k} = \frac{\partial}{\partial w_k} \sum_E \beta(E) \sigma^2\left(\frac{I_E}{\langle I_E \rangle}\right)$$

$$= \frac{\partial}{\partial w_k} \sum_E \beta(E') \sigma^2\left(\frac{I_{E'}}{\langle I_{E'} \rangle}\right)$$

$$= \beta(E') \frac{4 w_k}{N_{E'} \langle I_{E'} \rangle^2}\left(I_k - \frac{\langle I_{E'}^2 \rangle}{\langle I_{E'} \rangle}\right),$$

which takes into account that the sampling point k is contained within the iso-energy layer E'. Accordingly, it is possible to make use of the fact that the derivation of the sum is not equal to zero only for the summand of the iso-energy layer E'. $N_{E'}$ is the number of sampling points within the iso-energy layer E'.

The derivation of the cost function F(I) is then:

$$\frac{\partial F(I)}{\partial w_k} = \frac{\partial}{\partial w_k}\left[\sum_i s_i (\Delta d_i(I))^2\right] + \alpha \beta(E') \frac{4 w_k}{N_{E'}\langle I_{E'}\rangle^2}\left(I_k - \frac{\langle I_{E'}^2\rangle}{\langle I_{E'}\rangle}\right),$$

where the sampling point k is located in the iso-energy layer E'.

Using the derivation of the cost function F(I), the cost function F(I) is minimized. An iterative approach may be used in which a next best solution candidate I(t+1) is calculated for a current tuple I(t) with the aid of the function value and the derivations of K.

A condition of low particle number dynamics is incorporated into the optimization of the particle number distribution I such that the condition does not have to be taken into account in retrospect, after the determination of the particle number distribution I has been completed. In an approach where the particle number distribution I is optimized without taking the particle number dynamics into account, and an adjustment of I to the desired low particle number dynamics is carried out subsequently, a deterioration in terms of the dose distribution results.

Figure 3:
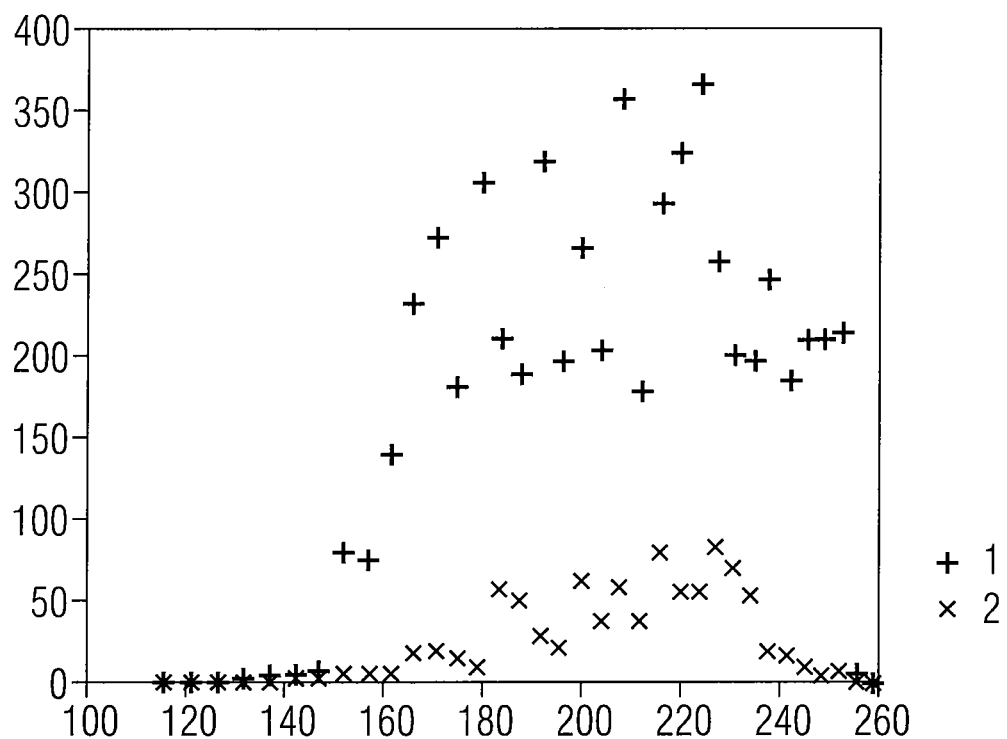
FIG. 3 shows example particle number dynamics for two different determined particle number distributions.

FIG. 3 shows one example of the effect of the optimization for a specific predefined target dose distribution. As shown in FIG. 3, the particle number dynamics are plotted on the y-axis, having been calculated as a particle number range (e.g., as a ratio of the highest particle number to the lowest particle number within an iso-energy layer). The different iso-energy layers or the associated starting energies of the particle are plotted in MeV on the x-axis. A curve 1, associated with the symbol +, corresponds to a determined particle number distribution I through optimization without taking the particle dynamics into account. The curve 2, associated with the symbol x, corresponds to a determined particle number distribution I through optimization in the above-described manner, taking the dynamics into account. FIG. 2 shows that the curve 2 has considerably better dynamic values and consequently, leads to a reduced irradiation time.

Figure 4A:
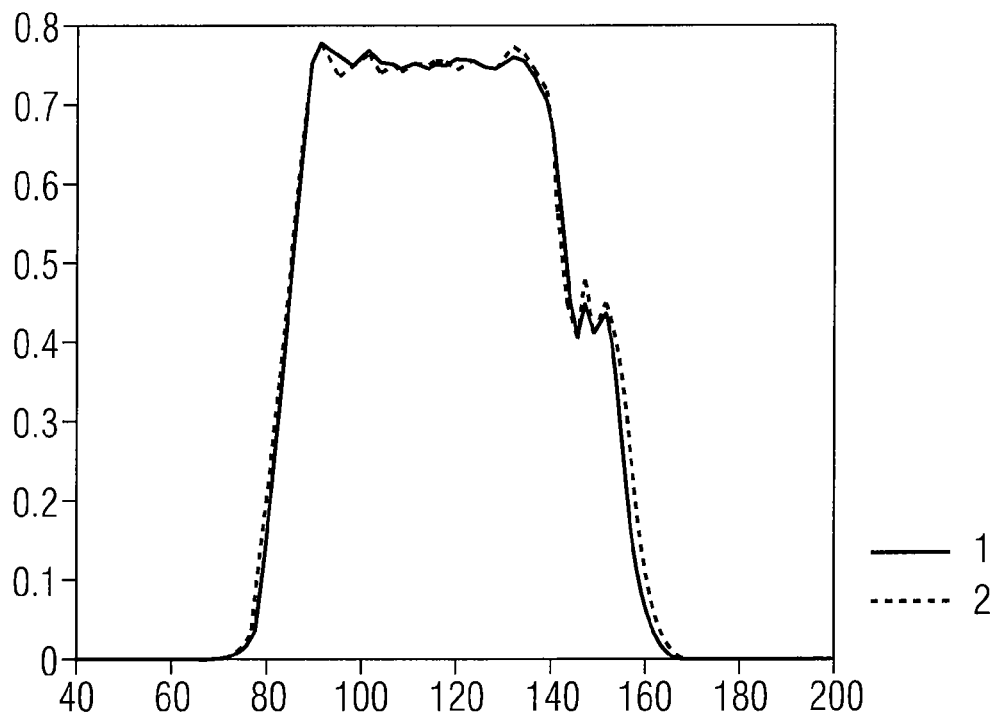
FIGS. 4A and 4B show example dose distributions for two different determined particle number distributions.
Figure 4B:
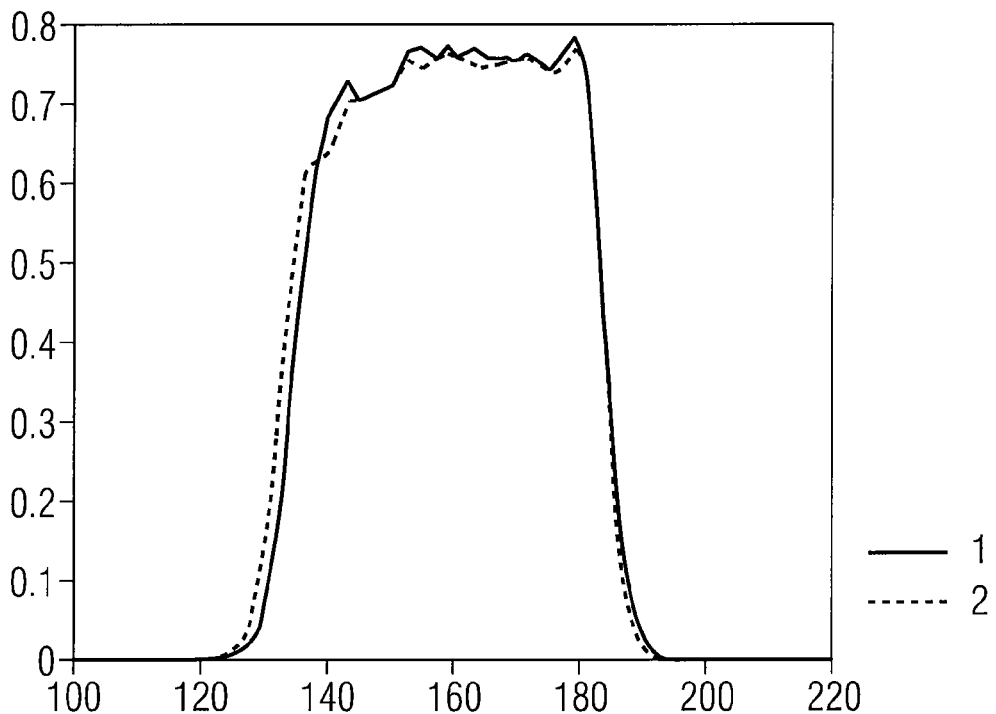

FIGS. 4A and 4B show the dose distributions resulting from the particle number distributions of the curve 1 and the curve 2 from FIG. 3, respectively. The dose is in each case plotted in Gray on the y-axes, while an intersection line along the irradiated object (e.g., a distance in mm) is plotted on the x-axis. FIGS. 4A and 4B correspond to two sections at right angles to one another through a dose distribution optimized for a cranial chordoma (a specific type of tumor). The unbroken curve 1, like the curve 1 of FIG. 3, corresponds to a determined particle number distribution I through optimization without taking the particle dynamics into account. In other words, the curve 1 corresponds to the predefined target dose distribution. The dashed curve 2, like the curve 2 of FIG. 3, corresponds to a determined particle number distribution I through optimization in the above-described manner, taking the dynamics into account. As shown in FIGS. 4A and 4B, the two curves do not diverge significantly from one another. By taking into account the particle number dynamics and consequently, the irradiation time, little deterioration is caused with respect to the dose distribution.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for determining control parameters for a particle irradiation system, the particle irradiation system being configured to dispose different dose values at different sampling points in a target volume, the target volume comprising a plurality of isoenergy layers, each isoenergy layer of the plurality of isoenergy layers being associated with a different particle beam energy, the device comprising:
   an input operable to receive information relating to a predefined dose distribution via target points; and
   a determination component operable to determine a particle number distribution to be deposited during an irradiation via sampling points,
   wherein the determination component is configured to determine the particle number distribution using the predefined dose distribution and a variable taking differences in the particle number distribution between particle numbers of different sampling points associated with the same isoenergy layer of the plurality of isoenergy layers into account, with the variable, the different sampling points being compared in terms of corresponding article numbers, each isoenergy layer of the plurality of isoenergy layers characterizing a penetration depth of particles having the associated particle beam energy.

2. The device as claimed in claim 1, wherein the variable takes differences between particle numbers of all sampling points, which, according to the particle number distribution, are to be irradiated with particles of the same energy, into account.

3. The device as claimed in claim 1, wherein the variable includes a scatter of particle numbers of different sampling points, which, according to the particle number distribution, are to be irradiated with particles of the same energy.

4. The device as claimed in claim 1, wherein the variable comprises a variance of particle numbers of different sampling points, which, according to the particle number distribution, are to be irradiated with particles of the same energy.

5. The device as claimed in claim 1, wherein the variable comprises a value range of particle numbers of different sampling points, which, according to the particle number distribution, are to be irradiated with particles of the same energy.

6. The device as claimed in claim 1, wherein the variable comprises a maximum difference of particle numbers of all sampling points, which, according to the particle number distribution, are to be irradiated with particles of the same energy.

7. The device as claimed in claim 1, wherein the variable comprises a ratio between a highest and a lowest particle number of all sampling points, which, according to the particle number distribution, are to be irradiated with particles of the same energy.

8. The device as claimed in claim 1, wherein the determination component is operable to determine the particle number distribution through optimization of a cost function, and
   wherein the cost function comprises a first term relating to the predefined dose distribution and a second term relating to the variable.

9. The device as claimed in claim 8, wherein the cost function further comprises a predefinable parameter for relative weighting of the first term compared to the second term.

10. The device as claimed in claim 8, wherein the optimization of the cost function optimizes the particle number distribution with respect to the predefined dose distribution and an irradiation duration.

11. The device as claimed in claim 1, wherein the variable includes a scatter of particle numbers of different sampling points, which, according to the particle number distribution, are to be irradiated with particles of the same energy.

12. The device as claimed in claim 2, wherein the variable comprises a variance of particle numbers of different sampling points, which, according to the particle number distribution, are to be irradiated with particles of the same energy.

13. The device as claimed in claim 4, wherein the determination component is operable to determine the particle number distribution through optimization of a cost function, and
   wherein the cost function comprises a first term relating to the predefined dose distribution and a second term relating to the variable.

14. The device as claimed in claim 1, wherein with the variable, the different sampling points are compared in relation to each other in terms of the corresponding particle numbers.

15. The device as claimed in claim 1, wherein the comparison comprises a mathematical difference.

16. A particle irradiation system configured to dispose different dose values at different sampling points in a target volume, the target volume comprising a plurality of isoenergy layers, each isoenergy layer of the plurality of isoenergy layers being associated with a different particle beam energy, the particle irradiation system comprising:
   a device operable to determine control parameters, the device comprising:
      an input operable to receive information relating to a predefined dose distribution via target points; and
      a determination component operable to determine a particle number distribution to be deposited during an irradiation via sampling points,
   wherein the determination component is configured to determine the particle number distribution using the predefined dose distribution and a variable taking differences in the particle number distribution between particle numbers of different sampling points associated with the same isoenergy layer of the plurality of isoenergy layers into account, with the variable, the different sampling points being compared in terms of corresponding particle numbers, each isoenergy layer of the plurality of isoenergy layers characterizing a penetration depth of particles having the associated particle beam energy.

17. A method for determining control parameters for a particle irradiation system, the method comprising:
   receiving information relating to a predefined dose distribution via target points; and
   determining, using a processor, a particle number distribution to be deposited during the irradiation via sampling points in a target volume, the target volume comprising a plurality of isoenergy layers, each isoenergy layer of the plurality of isoenergy layers being associated with a different particle beam energy,
   wherein the determining comprises using the predefined dose distribution and a variable taking differences in the particle number distribution between particle numbers of different sampling points associated with the same isoenergy layer of the plurality of isoenergy layers into account, with the variable, the different sampling points being compared in terms of corresponding particle numbers, each isoenergy layer of the plurality of isoenergy layers characterizing a penetration depth of particles having the associated particle beam energy.

18. A method for irradiating a target volume with particles using control parameters to control a particle irradiation system, the method comprising:
 determining the control parameters, the determining comprising:
  receiving information relating to a predefined dose distribution via target points;
  determining, using a processor, a particle number distribution to be deposited during the irradiation via sampling points in a target volume, the target volume comprising a plurality of isoenergy layers, each isoenergy layer of the plurality of isoenergy layers being associated with a different particle beam energy; and
  using the predefined dose distribution and a variable taking differences in the particle number distribution between particle numbers of different sampling points associated with the same isoenergy layer of the plurality of isoenergy layers into account, with the variable, the different sampling points being compared in terms of corresponding particle numbers, each isoenergy layer of the plurality of isoenergy layers characterizing a penetration depth of particles having the associated particle beam energy.

19. The method as claimed in claim 18, wherein the target volume comprises at least a sub-region of a non-living body for the purpose of verifying an irradiation plan.

20. In a non-transitory computer-readable storage medium having stored therein data representing code executable by a programmed computer for determining control parameters for a particle irradiation system, the storage medium comprising instructions for:
 receiving information relating to a predefined dose distribution via target points; and
 determining a particle number distribution to be deposited during the irradiation via sampling points in a target volume, the target volume comprising a plurality of isoenergy layers, each isoenergy layer of the plurality of isoenergy layers being associated with a different particle beam energy,
 wherein the determining comprises using the predefined dose distribution and a variable taking differences in the particle number distribution between particle numbers of different sampling points associated with the same isoenergy layer of the plurality of isoenergy layers into account, with the variable, the different sampling points being compared in terms of corresponding particle numbers, each isoenergy layer of the plurality of isoenergy layers characterizing a penetration depth of particles having the associated particle beam energy.

* * * * *